(12) United States Patent
Bennett, II

(10) Patent No.: US 7,967,729 B2
(45) Date of Patent: Jun. 28, 2011

(54) PHYSICAL THERAPY SYSTEM AND METHOD

(76) Inventor: Harold H. Bennett, II, Kirkland, WA (US)

(*) Notice: Subject to any disclaimer, the term of this patent is extended or adjusted under 35 U.S.C. 154(b) by 392 days.

(21) Appl. No.: 12/057,247

(22) Filed: Mar. 27, 2008

(65) Prior Publication Data
US 2008/0243038 A1   Oct. 2, 2008

Related U.S. Application Data

(60) Provisional application No. 60/908,364, filed on Mar. 27, 2007.

(51) Int. Cl.
*A63B 71/00* (2006.01)
(52) U.S. Cl. ........ 482/8; 482/1; 482/9; 482/51; 482/901
(58) Field of Classification Search .................. 482/1–9, 482/51, 900–902; 434/247
See application file for complete search history.

(56) References Cited

U.S. PATENT DOCUMENTS

| | | | | |
|---|---|---|---|---|
| 3,973,251 A * | 8/1976 | Stephans | .................... | 340/309.7 |
| 4,714,244 A * | 12/1987 | Kolomayets et al. | ............ | 482/72 |
| 5,020,794 A * | 6/1991 | Englehardt et al. | ................ | 482/5 |
| 5,667,459 A * | 9/1997 | Su | ..................... | 482/4 |
| 7,094,184 B1 * | 8/2006 | Chen et al. | ....................... | 482/93 |
| 7,717,827 B2 * | 5/2010 | Kurunmaki et al. | ............... | 482/8 |
| 7,727,117 B2 * | 6/2010 | Feldman et al. | .................. | 482/8 |
| 2003/0171190 A1 * | 9/2003 | Rice | ................. | 482/57 |

* cited by examiner

*Primary Examiner* — Glenn Richman
(74) *Attorney, Agent, or Firm* — Harold H. Bennett

(57) ABSTRACT

A system and method for developing an individual's physical abilities includes measuring one or more physical ability of an individual and establishing control parameters of a game such that operation of the game at a beginning level is within the individual's measured physical ability. The degree of physical ability shown by the individual over time of game play is monitored, and the control parameters are gradually modified to require a progressively greater physical ability of the individual than required at the beginning level. The system includes an input device, e.g., a joystick, that is operated by the individual to play the game. The system records aspects related to game play, such as frequency and duration of play, specific actions or motions, and changes in physical ability. A therapist is then able to review the record and modify system settings to optimize improvement by the individual.

16 Claims, 1 Drawing Sheet

PHYSICAL THERAPY SYSTEM AND METHOD

CROSS-REFERENCE TO RELATED APPLICATION

This application claims the benefit of U.S. Provisional Patent Application No. 60/908,364 filed Mar. 27, 2007 which is incorporated herein by reference in its entirety.

BACKGROUND OF THE INVENTION

1. Technical Field

This invention relates to the field of physical therapy and in particular to the use of physical therapy in the treatment of individuals with nerve damage or nerve impairment. In particular to the use of a software and hardware interface device in the use of therapy.

2. Description of the Related Art

Physical injuries often cause limited motion to the person injured. For example, an impact as may incur in a football game, car accident or other accident may cause damage to the nerves that control the arms of an individual. It has been shown that extensive exercise, along with other physical therapy can be extremely helpful in reestablishing control of the individual muscles and helping to stimulate the healing and recovery of the patients.

Various physical therapy regimes currently exist in order to aid a person having damage that limits their muscle control. The physical therapy includes such things as encouraging the patient to work certain muscles, move their arm or hands or other digits in certain manners, as well as other well-known techniques published in the art.

Physical therapists currently provide significant assistance to patients recovering from such accidents and injuries. Normally, physical therapists will work with the patient two or three times a week, conducting a one or two hour physical therapy session with the patient. During this session, the physical therapist assesses the individual patient's range of motion and strength. In addition to the assessment, the physical therapist will then outline a preferred set of exercises in order for the patient to gain further control and finer tune movement of the various muscle groups which have been affected by the injury. Normally, the physical therapist will provide an exercise regimen for the patient to undergo while the physical therapist is not present. It is quite common for the physical therapist to demonstrate the exercises to the patient and coach her in their execution to ensure that the patient understands them properly, and then request that the she carry out the exercise a number of times each day. For example, the patient might be instructed to move an arm through a certain range of movement ten times for ten repetitions at three separate times during the day. During the next visit, the physical therapist will assess the current status of the patient and whether she has improved her range of motion. The physical therapist will then make a determination whether the patient should continue the current exercise or whether the patient has progressed to the point where additional exercises should now be prescribed in order to provide further improvement for the patient. The physical therapist will continue to work with the patient, prescribing advancing sets of exercise regimens in order to provide greater and greater challenges in order to restore her limbs to full mobility.

Unfortunately, the physical therapist does not currently have a way to easily monitor the exercises that the patient performs during the time between visits. Further, the amount of effort put into the exercises cannot be easily measured without the use of expensive exercise and tracking equipment which may include some extensive sensors which must be customized to each individual patient and thus are cost prohibitive.

DETAILED DESCRIPTION

Figure 1:
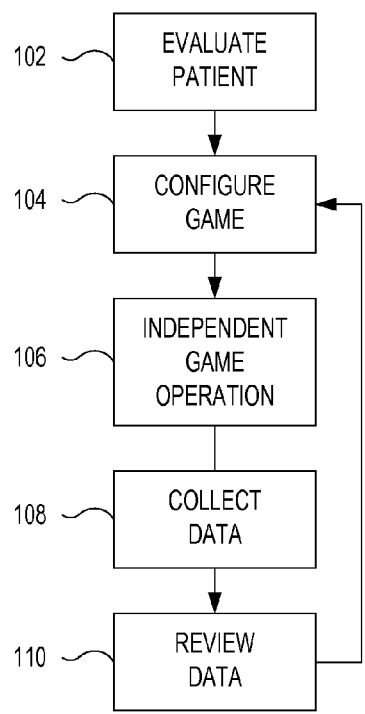
FIG. 1 shows a simple flow chart outlining the operation of a video game system according to an embodiment of the invention.

In the field of physical therapy one of the major challenges is motivating patients to do exercises that may be painful, difficult, or boring. According to the principles of the invention, an interface device, such as, for example, a joystick, is provided, which has sensors on it that not only sense motion in the X and Y axis but also rotational motion around the Z axis, and pressure sensors under the fingers which can sense gripping pressure either on the part of the entire hand or individual fingers applying pressure. In conjunction with the operation of the joystick a software program or software package is provided which incorporates one or more video games which are controlled at least partially through the use of the joystick.

In cases where the patient cannot grip the joystick, the joystick is configured such that the patient's hand is strapped thereto so as to be responsive to large motor movements of the hand or forearm. The joystick may be mounted to a larger substrate such as the arm of a chair, and the patient may be strapped at the upper arm to the chair to hold her arm in position to operate the joystick.

According to an embodiment, a tight-fitting glove is worn by the patient, which is then attached to the joystick, thereby positioning each of the patient's fingers for correct operation of the joystick. The palm surface of the glove and front surfaces of each finger are configured to removably adhere to the joystick. Velcro® may be used for this purpose, or some other attachment means. Alternatively, each finger of the glove is provided with a separate strap that firmly positions the respective finger on the joystick. According to another embodiment, the glove is provided with pressure sensors to detect grip force from each finger, independent of the joystick.

The video games are configured in a manner similar to many common video games, which are organized in levels, and in which the player or the operator, by performing a certain number of tasks or challenges, is able to progress from a lower level to a higher level. There may be many levels of operation. A player may be required to negotiate mazes, or vanquish enemies, or steer a vehicle. While playing a game, a player may obtain particular weapons or abilities; the player may acquire immunity from some menace; and the player may obtain points or other advantages by successful completion of particular tasks.

According to an embodiment, the games are structured to begin by requiring a minimal movement on the part of joystick in operation and as the levels progress the motions required will increase. Before a game is initiated the patient undergoes an evaluation, preferably by a trained therapist, but which may also be done automatically by the game software, in which the patient is prompted to make a series of movements with the joystick. The software measures the patient's range of motion and strength associated with each motion. The therapist or the evaluation software then adjusts the video game so that, at the lowest levels of the game, the functions of the game are controllable by the patient at his or her current level of ability. As the game progresses, the patient is encouraged to exercise the full range of motion that she then possesses, but will be further encouraged to develop other skills and abilities. For example, in an early stage of the game the patient may only be capable of a forward and back motion of the joystick. Under such circumstances the operation of the game would require at that level only forward and backward motions of the joystick. As the patient strives to progress from that level to the next, other motions would be encouraged, and as she begins to acquire additional mobility, such as, for example a right and left motion, the game would reward the patient with points, shortcuts, or other elements that are advantageous within the environment of the particular game.

Depending on the particular disability or injury, the patient may be subject to repeated involuntary movements or tremors. In such cases, the video game is adjusted to ignore such movements within limits established during evaluation, and to differentiate between those involuntary movements and similar movements that are voluntary. If the therapist has established, as a goal for the patient, improved control over such involuntary movements, the software may progressively lower the thresholds within which such movements are ignored. Thus, at a lower level of the game, the game ignores all such movements, but at higher levels, the patient must exert some control to reduce the involuntary movements to avoid provoking unintentional actions in the game.

In contrast to repeated involuntary movements, other actions or movements may occur spontaneously for the first time as the patient progresses. It may be important to detect and encourage such movements. Accordingly, as the patient is motivated to strive for higher scores and to advance to higher levels, the game rewards such spontaneous motions. For example, an individual who has only partial control over motions of his hands, might accidentally perform a movement that he is not striving to do, and has not previously been able to do. Under such circumstances the software recognizes and rewards the movement. Because the patient may be unaware of the movement, the software can be configured to pause the game to notify him of the detected movement. The software then provides an additional parameter of control that the patient can use in the game, but requires that he repeat the movement in order to exercise that control. Higher levels of the game require higher degrees of control, higher degrees of grip strength, and better small muscle control. Preferably, the game is configured to be modified by a physician or a physical therapist so that the game can be very closely tailored to the needs of the particular individual.

In the event that the practitioner believes or establishes that the degree of progress that this patient may make is limited, then the amount of progress that each small improvement produces can be increased such that where under other circumstances the game might require a great deal of improvement and control over the joystick in a forward and back motion, under the more limited conditions of a more severely injured or limited patient, the game will reward very small motions and very small improvements in motion with higher scores and higher advancement. By doing this the game can encourage small improvements in the case where a patient is not realistically expected to make a great deal of improvement or encourage greater improvement in cases where it is hoped that a fuller recovery or greater improvement might be expected. Similarly, a therapist may choose to provide the patient with a number of games sequentially over an extended period of time, each game being programmed to produce a small advance over the previous game, in order to achieve, overall, a significant improvement. Alternatively, the therapist may provide a number of games for the patient to work with concurrently, each, perhaps, tailored to address specific exercise goals, to provide the patient with some variety, and to allow the therapist to determine what sorts of games are most likely to be of interest to the patient and therefore to provide the most incentive to exercise.

The system is configured to track and record a number of parameters related to the patient's use of the game, such as, for example, the dates and times during which the game is used, the ranges of motion employed by the patient in operating the game, and improvements in strength, motion, and control achieved by the patient over a given time period. The therapist is then able to periodically evaluate the patient's progress. The therapist can determine whether the patient is regularly performing the prescribed exercises, how much effort is being expended in the exercises, and the degree of efficacy of the exercises. The therapist can then make adjustments to the system settings as necessary. For example, the therapist may note that the patient has acquired some additional mobility, but continues to favor the easier movements to play the game, even though the software has made other rewards available for using newer or more difficult movements. Under such circumstances, the therapist may change the weighting such that the easier movements become less useful as the player advances to higher levels, while the more difficult movements afford ever greater advantage in the game, thereby encouraging the patient to emphasize the more difficult movements. In a similar way, the therapist can modify control parameters of the game to address a wide range of specific exercise goals.

The flow chart of FIG. 1 illustrates a typical procedure. The therapist first evaluates the patient's existing range of motion, control, and strength 102, using a controller such as a joystick. The therapist then configures the game 104 to be operable, at least at its lowest level, by a player having the physical limitations of the patient, and sets forth the desired range of improvement, defined by the abilities necessary to operate the game at its highest level. The patient plays the game regularly over a period of time 106, during which the system collects data 108 regarding the patient's play and improvement. The resulting date is reviewed by the therapist 110, who determines what adjustments should be made to the game, or whether a new game should be introduced, to encourage further progress.

According to various embodiments, data may be tracked by the therapist via an internet connection, downloaded from the patient's unit to a storage medium and provided to the therapist for evaluation, or by other known methods of accessing and transmitting information. In some cases, it is possible for the practitioner to evaluate the patient's progress and make necessary revisions to the system solely from the collected data, without actually seeing the patient each time. This may be beneficial in cases, for example, where a patient, such as a young child, finds a visit to a therapist or physician to be particularly distressing, or where the patient lives a significant distance from the practitioner's office. It is only necessary to transmit the collected data to the practitioner, who can review the data, then transmit back any revisions to the game settings. In the case of a direct internet link between the patient's system and the therapist's, this interaction may be more or less continually ongoing, as the therapist can observe, even, perhaps, in real time, the patient's progress, and make minor adjustments as necessary.

Figure 2:
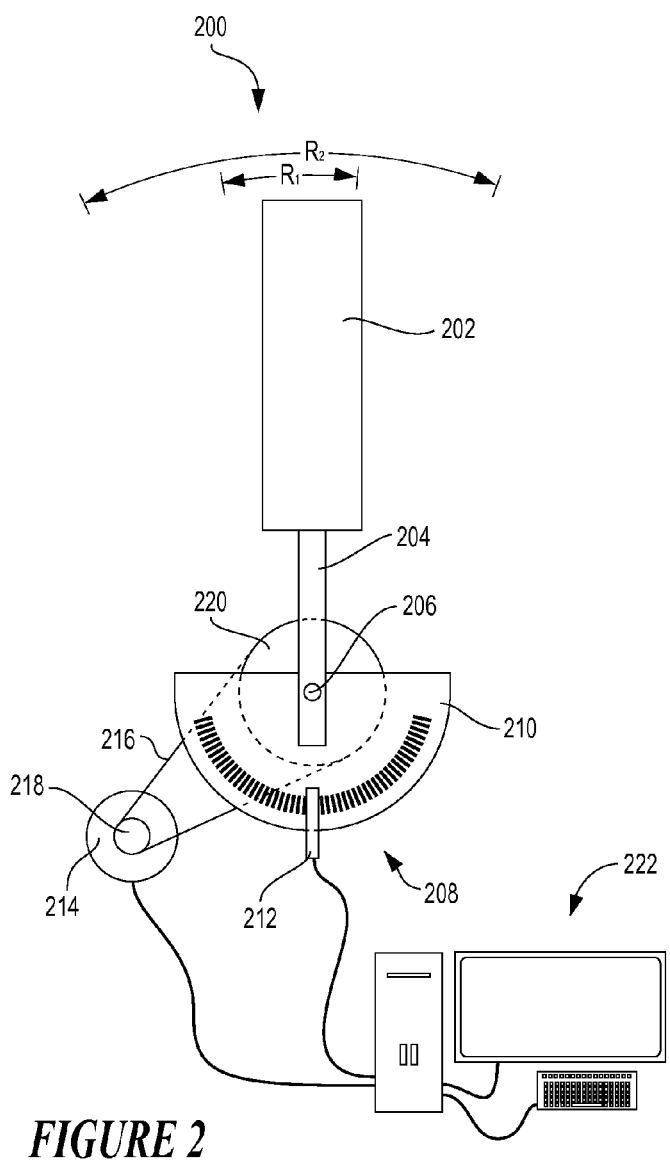
FIG. 2 is a diagrammatical representation of a game controller and computer system according to an embodiment.

Referring now to FIG. 2, a simplified joystick 200 is shown diagrammatically, showing elements associated with right and left movement of the joystick 200 only. The joystick 200 includes a handle, 202, a shaft 204, and a pivot point 206. An optical encoder 208, including a perforated disk 210, and an optical sensor 212, is coupled to the shaft and configured to detect the angular position of the handle 202. The joystick also includes an electric motor 214 coupled to the joystick 200 by a belt 216 extending between a first pulley 218 coupled to a rotor of the motor 214 and a second pulley 220 coupled to the shaft 204 of the joystick. A computer system 222 is coupled to the joystick to receive data from the optical encoder 208 and to control the polarity and torque of the motor 214. The joystick handle is configured to be rotatable about 75° in each direction from the center position, or neutral shown in the drawing. Elements such as joysticks, including optical encoders and motors for feedback, are well known in the art, and so need not be described in greater detail. The computer system 222 is provided with a software program configured to operate as described hereafter.

In operation, a patient is first instructed to grasp the handle 202 and rotate it to the right and left through her full range of motion in each direction. By repeating this action with the motor being controlled to exert increasing levels of resistance, her strength and absolute range of motion is measured and recorded by the computer system 222.

In the example shown, the patient is initially limited to a range $R_1$ of about 10° rotation to the left and 5° to the right, as shown at $R_1$, with little strength. The practitioner then designates a game function associated with left and right rotation of the joystick. If, hypothetically, the game includes a character that a user directs through a maze, and the right and left rotation of the joystick is designated to control rotation of the character's head to look right and left through 180°, the practitioner directs the program to proportionally correlate 10° of left rotation of the joystick to 90° of left rotation of the character's head, and 5° of right rotation of the joystick to 90° of right rotation of the character's head. The software program can also be directed to apply a selected resistance to rotation. In the present example, the resistance is initially set very low. Thus, when first playing the game, the patient is able to direct the on-screen character to rotate its head through 180°, even though she has only a limited range of motion herself. The practitioner may direct the program to progressively increase the range of motion necessary to rotate the character's head through its full range, or alternatively, the program may be directed to continually monitor the actual rotation range employed by the patient as she plays, and to increase the range of motion to the maximum rotation she exhibits. Additionally, the program may be directed to gradually increase the force necessary to move through the full range of motion, as described elsewhere.

As the patient progresses through various levels of the game, continually rotating the joystick to look left or right, her initial available range of 180° may gradually narrow as the program gradually increases the range of motion necessary to rotate the character's head, such that, without necessarily being aware of it, she continually strives to move beyond her current ability. In the alternative, she may gradually experience an increased range of motion, which will be detected by the computer system and software program, and in response to which the program will require her use of her full range to maintain full control over the character. Over the course of weeks or months of game play, she may increase her initial range $R_1$ to an expanded range $R_2$, and may not even be aware of the gradual improvement.

The embodiment disclosed with reference to FIG. 2 is provided to illustrate one simple example of some of the principles of the invention. In actual operation, a typical joystick would include at least two degrees of control, and might have three or more. The rotation sensor is described as an optical encoder, but one of ordinary skill will recognize that a wide range of analog and digital sensors may be used. Some embodiments will include controllable resistance, as provided here by the motor 212; others will not. All such parameters are subject to design considerations and the requirements of a particular application.

According to an embodiment, a second game controller or joystick is provided. The patient sits in a chair with two hands engaging two separate joysticks at the same time, and the software is structured to respond to both of them. The patient might be required to move both hands simultaneously in similar motions, thus encouraging recovery from a stroke, for example. Some research suggests that where a stroke victim has lost substantial use of one side of the body, requiring the patient to attempt to perform mirror actions simultaneously with both hands, for example, helps retrain the patient's brain to control the affected hand. In such a situation, the software may require little or no motion from the affected side to successfully operate the game at lower levels, but will demand more and more use of the affected side as the player progresses through the levels.

Under other circumstances, it may be important to encourage the patient to use each hand independently of the other. In the case of some spinal injuries, for example, it is not uncommon for a patient to develop control and feeling in one limb more quickly than another. Under such circumstances the patient may be discouraged in trying to develop the less responsive limb. Accordingly, such a patient may be permitted, at lower levels, to operate the game with only one controller or joystick, but as the game progresses, operation of the other controller will become more and more important, with each hand being required to perform different functions.

According to an embodiment of the invention, a number of games are provided to appeal to a broad range of personal interests. For example, if the patient is a young child or pre-teen, the game may involve high energy activities, such as flying exercises, flight simulators and the like, war games, car race games, or other sports related games, etc., or may be designed to appeal to more intellectual interests such as, for example, art or architecture, words, numbers, or mathematics, graphic arts, designing or assembling clothing ensembles or hairdos, decorating a room, riding animals, etc. The specific focus of the game can be designed to accommodate any particular interest, gender, and age.

While the system has been described with reference to a joystick as a game controller, a wide variety of user interfaces may be employed with advantage, depending on the condition to be treated. For example, a device that responds to movements of a patient's head, forearms, legs, or feet may be used for treatment directed to the respective part of the body. In some cases, the therapist may wish to emphasize range of motion, in some, strength development, and in others, small motor control. For each of these areas of emphasis, different interface devices can be designed to measure and respond to the specific elements in question.

According to one embodiment, a semi-flexible panel is provided that is arranged to selectively extend a number of needle probes similar to those employed by a physician to test tactile sensitivity. The panel may be placed on a patient's body in areas where it is hoped the patient will develop new tactile sensitivity. For example, some spinal injury patients initially have limited or no use of arms or hands, and no tactile sensation below the neck or shoulders. In such a case, the panel may be place across the patient's shoulders. The patient may control the game through movement of inertial sensors in a head band, for example, and the software may provide clues, such as advance warning of an event, by extending a number of probes to contact the patient's skin. To the extent that the patient is able to detect such warnings, the patient may be able to overcome specific menaces or obstacles in the game. As the patient's sensitivity improves, the game may reduce the number of probes extended, thereby demanding more sensitivity to detect them, or may extend probes further away from areas where sensitivity was not lost.

According to an embodiment, an interface device is provided that is configured to develop strength and range of motion. It includes sensors configured to detect distance of movement from a neutral or default position, and variable resistance elements configured to exert a selectable resistance to movement of the patient. In operation to develop forward hand rotation, for example, the system can be programmed to apply a relatively high level of resistance to rotation away from, but close to, the neutral position, and to reduce the resistance in relation to a distance from neutral. Thus, as the patient rotates her hand away from neutral, a high degree of effort is required, thereby developing strength in a range where she already has motion but little strength. As she moves through that range, the resistance decreases at least at a rate that compensates for her diminishing strength near the limits of her range of motion. As she approaches those limits, the resistance drops to zero, or may actually go to a negative value, meaning that the device actually applies some small force in the direction of rotation to encourage further rotation. Additionally, as she moves back toward neutral, the system can apply resistance to movement in that direction as well, to develop the opposing muscle groups. The system may be programmed to increase force toward the neutral position, or decrease resistance of movement toward neutral, over time, to prevent the patient from moving to a high angle and being unable to return to neutral.

According to an embodiment, sensor arrays may be attached to a patient's body to detect nerve signals for operation of the game, either in combination with, or in place of the joystick. For example, in the case of an amputee who is learning to exert neural control for electronic operation of a prosthetic limb, a cuff having a matrix of sensors is attached to the limb stump or area where the prosthesis will be attached. Initially, the therapist may simply instruct the patient to attempt to move the nonexistent limb through a wide range of movements. Various sensors of the matrix will detect the nerve impulses during the exercise and map their locations and strengths on the patient's body. Each of the movements that produced a measurable signal can then be assigned a function in a game, whereupon the patient merely plays the game. The sensors can be configured to detect impulses that are far too weak to control the prosthesis, but by proper configuration of the settings of the game, the patient may be taught to produce the appropriate signals at will.

Once the patient achieves sufficient control over signal production, a game that provides an on-screen character can be introduced, in which the patient has control of a limb of that character that corresponds to the prosthesis, and that responds as the prosthesis will respond to the signals. In this way, not only does the patient train in a progressively more specific manner to control the prosthesis, but the therapist can determine where to place the sensors of the prosthesis to most effectively respond to the patient's commands.

According to an alternate embodiment, the sensor array is positioned to detect attenuated nerve impulses of a patient with nerve damage. In many nerve-damage cases in which patients have lost the use of a limb, the nerves continue to transmit nerve impulses, but at a level that is too low to produce a response from the target muscles. By sensing these diminished nerve signals and producing on-screen actions in response, such a patient may be able to reestablish or restore the damaged nerve path and regain use of the affected area.

According to an embodiment, the system is configured to permit interactive gaming. For example, the patient and another player are provided with separate controllers in order to compete against each other. The weighting of the system is adjusted to handicap one or the other of the players to allow a physically impaired player to compete successfully against a more able player. Such a system can be configured to operate as a stand-alone device, or may alternatively be configured to operate in cooperation with another similar system, or via an internet connection.

The system, according to various embodiments, may be based on a personal computer, a conventional game controller, or an apparatus designed and built specifically to operate as described. It will be recognized that components of the system may be remote from each other. For example, it is not necessary that the therapist have constant access to the controller, while the patient does not need access to the software by which the therapist reviews data and establishes control parameters. If so configured, the therapist can provide revisions to existing control parameters, which are then uploaded to the game system used by the patient.

According to an embodiment, the system includes a module that interfaces with a standard game system or computer and is adapted to convert the input signals provided by the patient, using whatever input device is appropriate, to standard control signals that are recognized by the controller or computer. In this way, a patient can play conventional video games while also obtaining some or all of the benefits described above with respect to other embodiments.

One of the greatest challenges faced by therapists is motivating patients to perform prescribed exercises while the therapist is not present. This is especially true with children, who are more likely to become discouraged when there is little or no immediate perceptible progress. A child may avoid pushing an exercise to the point where it will actually result in improvement, because of difficulty, pain, or boredom, but may also learn to simulate effort in order to satisfy a parent or therapist. This is dangerous because, as is well known in the case of many types of injuries, significant improvement may be possible if concerted work is put forth immediately following the injury, while the same degree of work, applied later, will not have the same effect. Thus, a significant degree of potential recovery may be lost because the child cannot be persuaded to put forth early and serious effort. There is, therefore, a need for a means to provide a strong incentive to regularly perform prescribed exercises, for all patients, but especially for children.

In a case where the patient is an adult, with little or no interest in video games, the principles of the invention may be applied to operation of other aspects of a computer such as, for example, word processing programs, spread sheets, and web browsing. Operational control can be established within the abilities of the patient, but, over time, the system may gradually and, perhaps imperceptibly, require more of the patient. New or improved abilities can be rewarded with more efficient operation of the system, and the system can be tailored to demand a degree of effort commensurate with the expectations of the therapist.

Where the claims use the term game, this is to be read broadly on elements that are controllable by computer or microprocessor, including video games, simulators, web browsers, word processors, spread sheets, etc.

Where the claims use the term level, this is to be read on a point of progression in the game. It is not limited to discrete levels that are found in many video games, and often referenced by number.

The abstract of the present disclosure is provided as a brief outline of some of the principles of the invention according to one embodiment, and is not intended as a complete or definitive description of any embodiment thereof, nor should it be relied upon to define terms used in the specification or claims. The abstract does not limit the scope of the claims.

From the foregoing it will be appreciated that, although specific embodiments of the invention have been described herein for purposes of illustration, elements of the various embodiments described above can be combined, and further modifications can be made, to provide further embodiments without deviating from the spirit and scope of the invention.

These and other changes can be made to the embodiments in light of the above-detailed description. In general, in the following claims, the terms used should not be construed to limit the claims to the specific embodiments disclosed in the specification, but should be construed to include all possible embodiments along with the full scope of equivalents to which such claims are entitled. Accordingly, the claims are not limited by the disclosure.

The invention claimed is:

1. A method, comprising:
    measuring a physical ability of an individual with respect to each of a plurality of separate movements;
    establishing control parameters of a game such that operation of the video game at a beginning level requires use by the individual of at least one of the plurality of separate movements, and is within the individual's measured physical ability with respect to the at least one movement;
    monitoring a degree of physical ability with respect to each of the plurality of separate movements shown by the individual over time of game play; and
    modifying the control parameters at a level above the beginning level to require a greater physical ability of the individual, with respect to the at least one movement, than required at the beginning level in order to obtain a same response from the game.

2. The method of claim 1 wherein the modifying includes modifying the control parameters of the game such that operation of the game at successive levels above the beginning level of the game require progressively greater physical ability in one or more of the plurality of separate movements.

3. The method of claim 2 wherein the modifying includes, at some level of the game, modifying the control parameters of the game such that operation of the game requires physical ability with respect to the at least one movement that exceed the individual's measured physical ability.

4. The method of claim 1, comprising collecting data relative to the individual's play of the game.

5. The method of claim 4, comprising evaluating the collected data and revising the control parameters of the game according to changes in the individual's physical ability as indicated by the collected data.

6. The method of claim 1 wherein the measuring includes measuring at least one range of motion of the individual's hand.

7. The method of claim 1 wherein the measuring includes measuring the individual's grip strength of one hand.

8. The method of claim 1 wherein the measuring includes measuring a level of strength of the individual with respect to one or more of the plurality of separate movements.

9. The method of claim 1, comprising setting parameters of a software program that performs the monitoring and the modifying.

10. The method of claim 9 wherein the setting comprises:
    evaluating results of the measuring;
    estimating a degree of improvement in physical ability possible by the individual while playing the game; and
    setting the parameters of the software to perform the modifying in a way that completion of the game requires the estimated degree of improvement.

11. The method of claim 9 wherein the setting comprises:
    evaluating results of the measuring;
    estimating a degree of improvement in physical ability possible by the individual; and
    setting the parameters of the software to perform the modifying in a way that is commensurate with the estimated degree of improvement.

12. The method of claim 9 wherein the setting comprises:
    setting the parameters of the software to perform the modifying as the monitoring detects increases in the individual's physical ability, to continually require a large portion of the individual's physical ability to play the game.

13. The method of claim 9 wherein the setting comprises:
    setting the parameters of the software to pause the game when the monitoring detects an increase in the individual's physical ability with respect to the at least one of the plurality of separate movements, and to notify the individual of the increased physical ability.

14. The method of claim 9 wherein the setting comprises:
    setting the parameters of the software to reward the individual when the monitoring detects an increase in the individual's physical ability with respect to one of the plurality of separate mmovements.

15. The method of claim 1 wherein:
    each of the plurality of separate movements are movements associated with an amputated limb of the individual;
    the measuring comprises detecting nerve signals associated with each of the plurality of separate movements; and
    the establishing comprises configuring the game to permit the individual to control a function of the game using nerve signals associated with the at least one movement.

16. The method of claim 1 wherein the modifying includes modifying the control parameters of the game such that, at a level above the beginning level, control of a function of the game is assigned to another of the plurality of separate movements not previously assigned to control a function.

* * * * *